(12) United States Patent
Foley

(10) Patent No.: US 9,880,226 B2
(45) Date of Patent: Jan. 30, 2018

(54) ESTIMATING COOLANT CONDUCTIVITY IN A MULTI-VOLTAGE FUEL CELL SYSTEM WITHOUT DISCONNECTING CONTACTORS

(71) Applicant: GM GLOBAL TECHNOLOGY OPERATIONS LLC, Detroit, MI (US)

(72) Inventor: Robert S. Foley, Rochester, NY (US)

(73) Assignee: GM Global Technology Operations LLC, Detroit, MI (US)

( * ) Notice: Subject to any disclaimer, the term of this patent is extended or adjusted under 35 U.S.C. 154(b) by 182 days.

(21) Appl. No.: 14/882,247

(22) Filed: Oct. 13, 2015

(65) Prior Publication Data

US 2017/0102432 A1    Apr. 13, 2017

(51) Int. Cl.
| | | |
|---|---|---|
| *G01R 31/36* | (2006.01) | |
| *B60L 11/18* | (2006.01) | |
| *G01R 27/22* | (2006.01) | |
| *G01N 27/06* | (2006.01) | |

(52) U.S. Cl.
CPC ...... *G01R 31/3648* (2013.01); *B60L 11/1892* (2013.01); *G01N 27/06* (2013.01); *G01R 27/22* (2013.01); *G01R 31/3662* (2013.01)

(58) Field of Classification Search
CPC ............... G01N 27/06; G01R 31/3648; G01R 31/3662; B60L 11/1892; H01M 8/04559
USPC ......................................... 324/430, 432, 426
See application file for complete search history.

(56) References Cited

U.S. PATENT DOCUMENTS

| | | | | |
|---|---|---|---|---|
| 7,906,242 B2 * | 3/2011 | Raiser | ............... | H01M 8/04537 429/428 |
| 9,068,922 B2 | 6/2015 | Foley | | |
| 2004/0265660 A1 * | 12/2004 | Reuschel | ................. | C09K 5/10 429/437 |
| 2005/0274676 A1 * | 12/2005 | Kumar | ..................... | B01J 47/04 210/681 |
| 2012/0064426 A1 * | 3/2012 | Sato | ..................... | B60L 11/1803 429/434 |
| 2014/0266223 A1 * | 9/2014 | Foley | ................ | H01M 8/04992 324/426 |

* cited by examiner

*Primary Examiner* — M'Baye Diao
(74) *Attorney, Agent, or Firm* — John A. Miller; Miller IP Group, PLC

(57) ABSTRACT

A system and method for monitoring the conductivity of a cooling fluid flowing in a fuel cell system on a vehicle including a chassis. The fuel cell system includes a fuel cell stack electrically coupled to a stack bus and a battery electrically coupled to a propulsion bus. The method includes operating the fuel cell system, measuring a first isolation resistance at the first power level, measuring a first stack voltage, and measuring a first battery voltage. The method also includes operating the fuel cell system at a second power level, and measuring a second isolation resistance, measuring a second stack voltage, and measuring a second battery voltage. The method calculates a stack coolant resistance using the first and second isolation resistances, the first and second stack voltages, and the first and second battery voltages, which is then used to calculate the cooling fluid conductivity.

8 Claims, 3 Drawing Sheets

ESTIMATING COOLANT CONDUCTIVITY IN A MULTI-VOLTAGE FUEL CELL SYSTEM WITHOUT DISCONNECTING CONTACTORS

BACKGROUND OF THE INVENTION

Field of the Invention

This invention relates generally to a system and method for estimating the conductivity of a cooling fluid flowing in a fuel cell system and, more particularly, to a system and method for estimating the conductivity of a cooling fluid flowing in a fuel cell system, where the method measures a positive to chassis isolation resistance at a high system power level, measures the positive to chassis isolation resistance at a low system power level, measures fuel cell stack voltage and battery voltage at the two power levels, and uses the two positive to chassis isolation resistances and the voltages to identify a stack coolant positive to chassis isolation resistance.

Discussion of the Related Art

A hydrogen fuel cell is an electro-chemical device that includes an anode and a cathode with an electrolyte therebetween. The anode receives hydrogen gas and the cathode receives oxygen or air. The hydrogen gas is dissociated in the anode to generate free hydrogen protons and electrons. The hydrogen protons pass through the electrolyte to the cathode. The electrons from the anode cannot pass through the electrolyte, and thus are directed through a load to perform work before being sent to the cathode. Proton exchange membrane fuel cells (PEMFC) are a popular fuel cell type for vehicles, and generally includes a solid polymer electrolyte proton conducting membrane, such as a perfluorosulfonic acid membrane. The anode and cathode typically include finely divided catalytic particles, usually platinum (Pt), supported on carbon particles and mixed with an ionomer, where the catalytic mixture is deposited on opposing sides of the membrane. The combination of the anode catalytic mixture, the cathode catalytic mixture and the membrane define a membrane electrode assembly (MEA).

Several fuel cells are typically combined in a fuel cell stack to generate the desired power. A fuel cell stack typically includes a series of flow field or bipolar plates positioned between the several MEAs in the stack, where the bipolar plates and the MEAs are positioned between two end plates. The bipolar plates include an anode side and a cathode side for adjacent fuel cells in the stack. Anode gas flow channels are provided on the anode side of the bipolar plates that allow the anode reactant gas to flow to the respective MEA. Cathode gas flow channels are provided on the cathode side of the bipolar plates that allow the cathode reactant gas to flow to the respective MEA. One end plate includes anode gas flow channels, and the other end plate includes cathode gas flow channels. The bipolar plates and end plates are made of a conductive material, such as stainless steel or a conductive composite. The end plates conduct the electricity generated by the fuel cells out of the stack. The bipolar plates also include flow channels through which a cooling fluid flows.

Most fuel cell vehicles are hybrid vehicles that employ a supplemental power source in addition to the fuel cell stack, such as a high voltage DC battery or an ultracapacitor. A DC/DC converter is typically employed to match the stack voltage to the voltage of the battery. The power source provides supplemental power for the various vehicle auxiliary loads, for system start-up and during high power demands when the fuel cell stack is unable to provide the desired power. The fuel cell stack provides power to an electrical traction motor through a DC high voltage electrical bus for vehicle operation. The battery provides supplemental power to the electrical bus during those times when additional power is needed beyond what the stack can provide, such as during heavy acceleration. For example, the fuel cell stack may provide 70 kW of power, however, vehicle acceleration may require 100 kW of power. The fuel cell stack is used to recharge the battery or ultracapacitor at those times when the fuel cell stack is able to provide the system power demand. The generator power available from the traction motor during regenerative braking is also used to recharge the battery or ultracapacitor.

It is necessary to provide control algorithms on a fuel cell hybrid vehicle to determine how much power will be provided by the fuel cell stack and how much power will be provided by the battery in response to a driver power request and under all vehicle operating conditions. It is desirable to optimize the power distribution provided by the fuel cell stack and the battery so that the amount of hydrogen used to operate the vehicle is minimized. In other words, it is desirable to operate the fuel cell system in the most efficient manner that allows the vehicle to travel the farthest distance using the least amount of hydrogen. The battery must be operated within a defined state-of-charge (SOC) range, where the control algorithms typically provide a SOC set-point to which the battery charge and discharge is controlled based on that set-point.

In order to provide safe operation of a fuel cell hybrid vehicle, all high voltage parts of the electrical system on the vehicle need to be electrically isolated from the vehicle chassis. One way of providing high voltage isolation is to maximize one or more of the isolation resistances that limit the current flow to the chassis from a high voltage source, as is well understood by those skilled in the art. The loss of high voltage isolation between the vehicle electrical system and the vehicle chassis must be detectable during vehicle operation. When a high voltage isolation fault is detected, the isolation fault detection system will take suitable action, such as shutting down the system or providing a warning light to the vehicle operator.

The cooling fluid flowing through cooling channels in the fuel cell stack to cool the bipolar plates could provide an electrical connection between the fuel cell stack and the vehicle chassis, such as at the cooling system radiator. Thus, the cooling fluid is designed to have a low conductivity. However, over time, impurities and other contaminants enter the cooling fluid as a result of age and wear on the system, where those contaminants increase the ions in the cooling fluid making it more conductive. Also, as the cooling fluid is continually heated and cooled, it breaks down, also increasing its conductivity. Therefore, the cooling fluid needs to be periodically replaced so that it is not a cause of loss of high voltage isolation. Detecting for the loss of high voltage isolation may indicate that loss of isolation has occurred that could be caused by an increased conductivity of the cooling fluid before its next scheduled replacement. When loss of high voltage isolation is detected, a service technician will typically have to isolate components from the high voltage bus to determine the cause of the isolation fault, which is time consuming and labor intensive. If the technician knew that it was the conductivity of the cooling fluid causing the fault, then the cooling fluid could be replaced without having to test all of the other components in the high voltage system.

SUMMARY OF THE INVENTION

The present invention discloses and describes a system and method for estimating the conductivity of a cooling fluid flowing in a fuel cell system on a vehicle that does not require closing and opening of contactors. The fuel cell system includes a fuel cell stack electrically coupled to a stack bus and a battery electrically coupled to a propulsion bus, where the stack bus and the propulsion bus operate at different voltage potentials. The method includes operating the fuel cell system at a first power level, measuring a first isolation resistance between the propulsion bus and vehicle chassis ground at the first power level, measuring a first stack voltage at the first power level, and measuring a first battery voltage at the first power level. The method also includes operating the fuel cell system at a second power level that is different than the first power level, and measuring a second isolation resistance between the propulsion bus and chassis ground at the second power level, measuring a second stack voltage at the second power level, and measuring a second battery voltage at the second power level. The method calculates a stack coolant resistance using the first and second isolation resistances, the first and second stack voltages, and the first and second battery voltages, which is then used to calculate the cooling fluid conductivity.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a system and method for determining the conductivity of a cooling fluid flowing through a fuel cell stack is merely exemplary in nature, and is in no way intended to limit the invention or its applications or uses.

Figure 1:
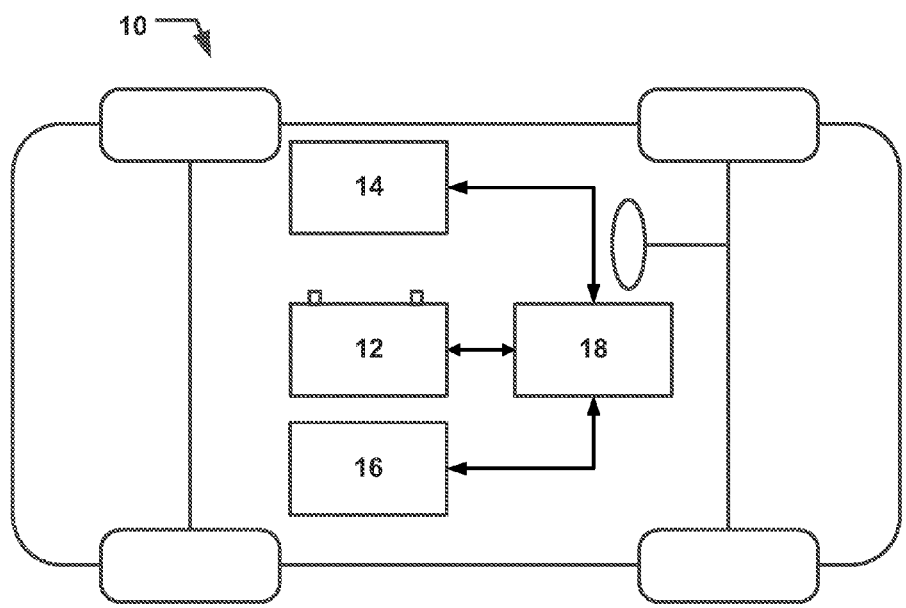
FIG. 1 is an illustration of a vehicle including a fuel cell system.

FIG. 1 is a simplified view of a hybrid fuel cell electric vehicle 10 that includes a high-voltage battery 12, a fuel cell stack 14, a propulsion unit 16 and a controller 18. The controller 18 represents all of the control modules, processors, memory and devices necessary for the operation and power flow control in the vehicle 10 as discussed herein.

Figure 2:
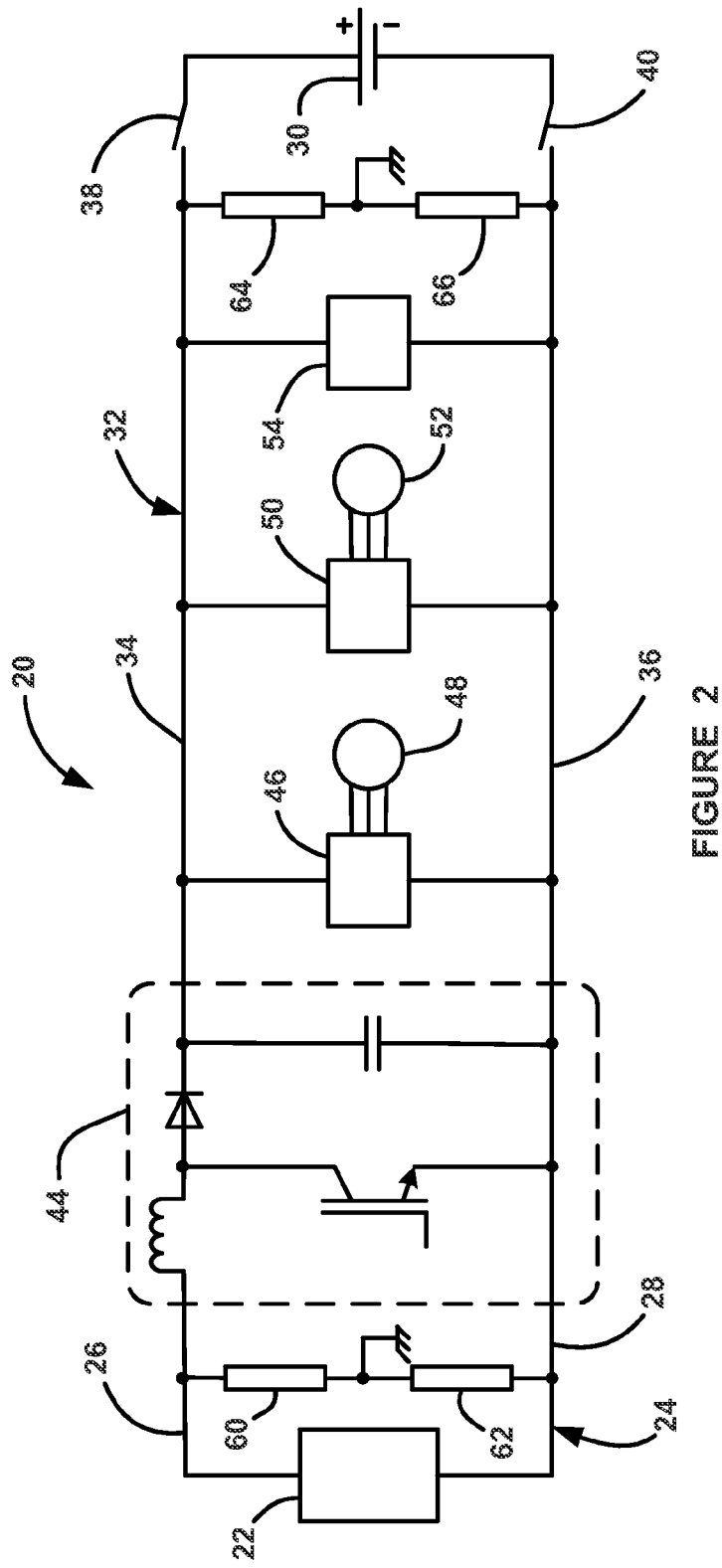
FIG. 2 is a schematic block diagram of a high-voltage architecture of a fuel cell system.

FIG. 2 is a schematic block diagram of a high-voltage architecture 20 for a fuel cell system, where the architecture 20 includes a fuel cell stack 22 electrically coupled to a stack bus 24 having a positive rail 26 and a negative rail 28, and a high voltage battery 30 electrically coupled to a propulsion bus 32 including a positive rail 34 and a negative rail 36, where electrical contactors 38 and 40 are coupled to the rails 34 and 36, respectively. The high voltage battery 30 can be any suitable rechargeable battery system that provides various desirable charging and discharging characteristics for fuel cell system applications, including, but not limited to, lithium-ion batteries, Ni-MH batteries, sodium-nickel-chloride batteries, lead-acid batteries, nickel-cadmium batteries, etc. Although the battery 30 is employed in this non-limiting embodiment as a supplemental power source, other high voltage DC storage devices can be employed instead of the battery 30, such as an ultracapacitor.

The stack bus 24 and the propulsion bus 32 are electrically separated by a DC/DC boost converter 44 that provides voltage matching between the stack 22 and the battery 30, and provides current control that selectively determines how much power is provided by the stack 22 to drive various system loads in a manner well understood by those skilled in the art. Voltages from the fuel cell stack 22 and the battery 30 power the various system loads, including a compressor power inverter module (CPIM) 46 and associated compressor motor 48, a power inverter module (PIM) 50 and associated traction motor 52 and other system loads 54 electrically coupled across the rails 34 and 36, as shown. The PIM 50 converts the DC voltage on the rails 34 and 36 to an AC voltage suitable for the AC traction motor 52. The traction motor 52 provides traction power to operate the vehicle 10, and can be any suitable motor for that purpose, such as an AC induction motor, an AC permanent magnet motor, an AC 3-phase synchronous machine, etc. For a typical hybrid vehicle strategy, the battery 30 is mainly used to increase efficiency, lower the dynamic requirements of the fuel cell system, and/or increase the performance of the vehicle 10. If the vehicle operator demands more power, the battery 30 can provide the stored energy to the traction motor 52 very fast.

The architecture 20 maximizes isolation resistances for high voltage protection and isolation in a manner well understood by those skilled in the art. Particularly, a positive to chassis stack isolation resistance element 60 is electrically coupled to the positive stack rail 26 and chassis ground, a negative to chassis stack isolation resistance element 62 is electrically coupled to the negative stack rail 28 and chassis ground, a positive to chassis propulsion bus isolation resistance element 64 is electrically coupled to the positive bus rail 34 and chassis ground, and a negative to chassis propulsion bus isolation resistance element 66 is electrically coupled to the negative bus rail 36 and chassis ground.

Figure 3:
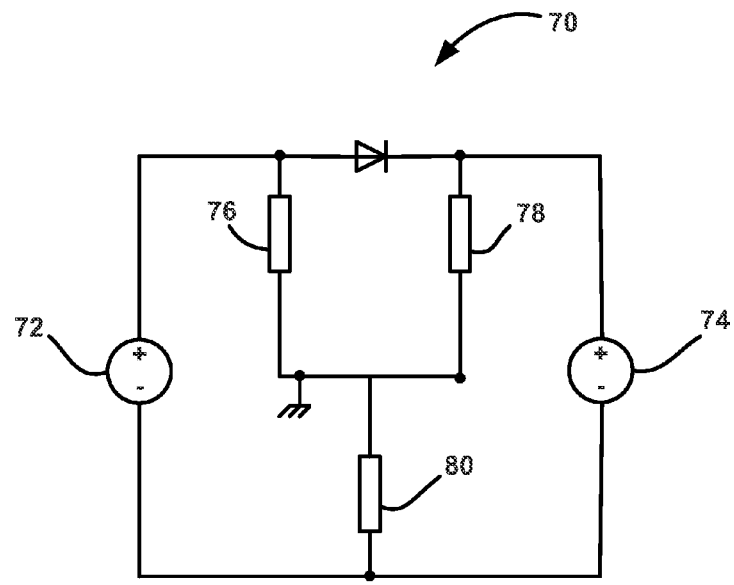
FIG. 3 is a simplified isolation resistance model of the high-voltage architecture shown in FIG. 2.

FIG. 3 is a schematic block diagram of an isolation resistance equivalent circuit model 70 of the architecture 20, and includes a DC source 72 representing the fuel cell stack voltage $V_s$ and a battery source 74 representing the battery voltage $V_b$. A resistance element 76 represents the parallel combination of all resistances connected from the positive terminal of the fuel cell stack 22 to ground, referred to herein as the fuel cell stack coolant positive to chassis isolation resistance $R_{pcs}$, and includes the positive to chassis stack isolation resistance element 60. A resistive element 78 represents the parallel combination of all resistances connected from the positive terminal of the battery 30 to ground, referred to herein as the propulsion bus positive to chassis isolation resistance $R_{pcb}$, and includes the positive to chassis propulsion bus isolation resistance element 64. A resistive element 80 represents the parallel combination of all resistances connected from the shared negative terminal to ground, referred to herein as the propulsion bus negative to chassis isolation resistance $R_{nc}$, and includes the negative to chassis stack isolation resistance element 62 and the negative to chassis propulsion bus isolation resistance element 66.

The isolation resistance equivalent circuit model 70 provides three possible current paths between the propulsion bus 32 to chassis ground. Thus, from the circuit model 70, an apparent positive to chassis isolation resistance $R_{pcPB}$ that is measured on the propulsion bus 32 can be defined as:

$$R_{pc_{PB}} = \cfrac{1}{\cfrac{1}{\left(\cfrac{V_b}{V_s}\right) \cdot R_{pcs}} + \cfrac{1}{R_{pcb}}}. \quad (1)$$

However, it is not known which part of the isolation resistance $R_{pc_{PB}}$ is from the positive propulsion bus resistance element 64 and which part of the isolation resistance $R_{pc_{PB}}$ is the resistance from the stack cooling fluid.

The ratio of battery voltage to stack voltage changes depending on the power being drawn from the system, where a high power request causes a low stack voltage and a high battery voltage and a low power request causes a high stack voltage and a low battery voltage. The present invention proposes calculating the fuel cell stack coolant positive to chassis isolation resistance $R_{pcs}$ by measuring the apparent positive to chassis isolation resistance $R_{pc_{PB}}$ for two different stack voltages $V_{s1}$ and $V_{s2}$, for example, a high stack voltage, which gives a corresponding battery voltage $V_{b1}$, and a low stack voltage, which gives a corresponding battery voltage $V_{b2}$, where the fuel cell stack coolant positive to chassis isolation resistance $R_{pcs}$ can be used to determine the cooling fluid conductivity.

By using the measured isolation resistance $R_{pc_{PB1}}$, the stack voltage $V_{s1}$ and the battery voltage $V_{b1}$ for one version of equation (1) and using the measured isolation resistance $R_{pc_{PB2}}$, the stack voltage $V_{s2}$ and the battery voltage $V_{b2}$ for another version of equation (1), those two equations can be solved to obtain the fuel cell stack coolant positive to chassis isolation resistance $R_{pcs}$ as:

$$R_{pcs} = \frac{R_{pc_{PB1}} \cdot R_{pc_{PB2}}}{R_{pc_{PB1}} - R_{pc_{PB1}}} \cdot \left(\frac{V_{s2}}{V_{b2}} - \frac{V_{s1}}{V_{b1}}\right). \quad (2)$$

It is noted that the isolation resistance $R_{pc_{PB}}$ can be measured in any suitable manner as would be well understood by those skilled in the art. For example, a known resistance value can be switched across the propulsion bus rail 36 and chassis ground in parallel with the isolation resistance 64 to set up a voltage divider network, where the value of the known resistance can be used to determine the value of the isolation resistance $R_{pc_{PB}}$. It is further noted that the fuel cell stack coolant positive to chassis isolation resistance $R_{pcs}$ can be defined by any suitable length or column of cooling fluid in the system, where an electrical potential can be obtained, such as, for example, between a last plate in the fuel cell stack 22 and a location where the cooling fluid pipe comes in contact with chassis ground, such as at a radiator.

Figure 4:
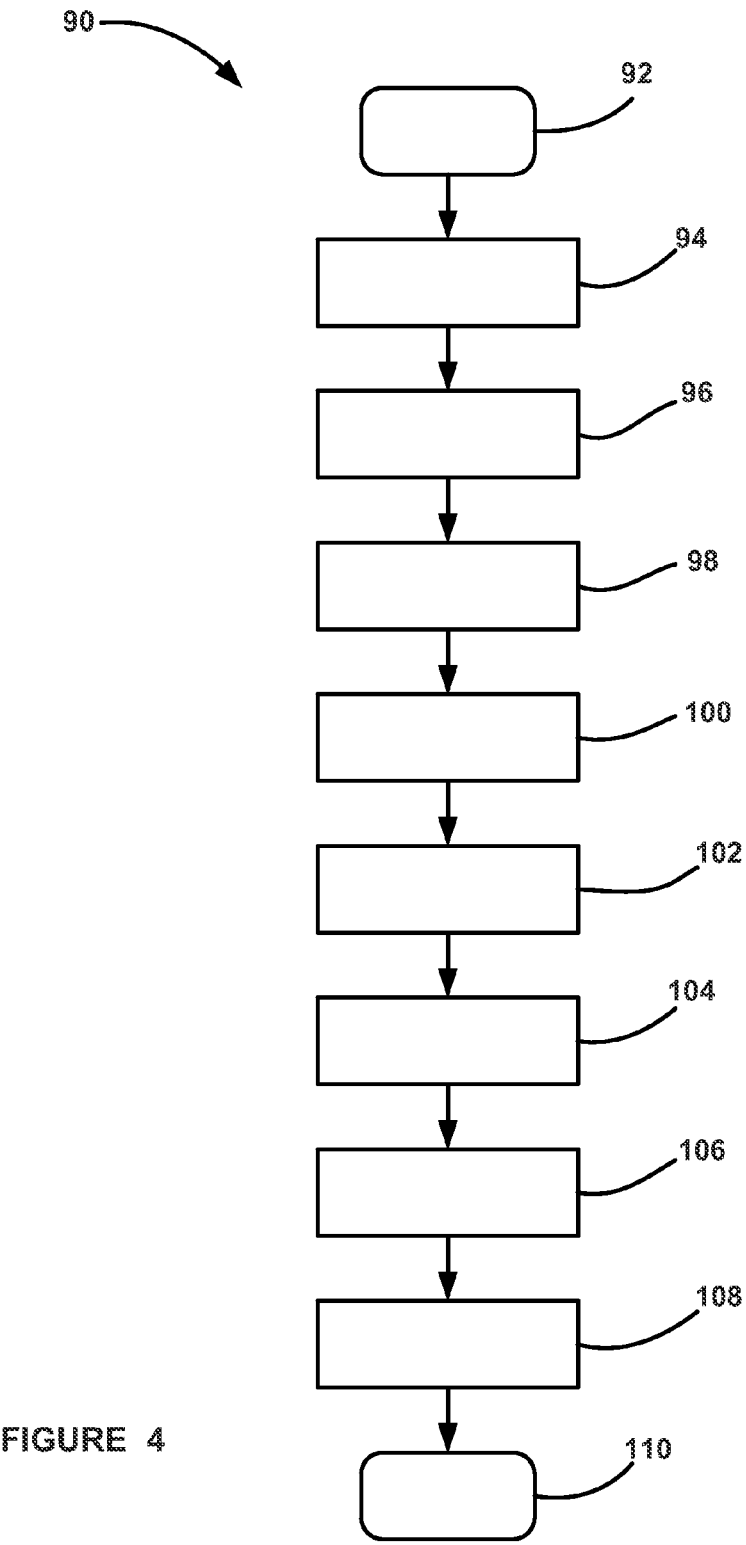
FIG. 4 is a flow chart diagram showing a process for determining conductivity of a cooling fluid in a fuel cell stack.

FIG. 4 is a flow chart diagram 90 showing the process discussed above for calculating the fuel cell stack coolant positive to chassis isolation resistance $R_{pcs}$. The process begins at box 92 and causes the fuel cell system to operate at high power at box 94. While the fuel cell system is being operated at high power, the process measures the high voltage apparent positive to chassis isolation resistance $R_{pc_{PB1}}$ at box 96. The process then measures the stack voltage $V_{s1}$ and the battery voltage $V_{b1}$ at box 98. The process then causes the fuel cell system to operate at low power at box 100, and measures the low voltage apparent positive to chassis isolation resistance $R_{pc_{PB2}}$ at box 102. The process then measures the stack voltage $V_{s2}$ and the battery voltage $V_{b2}$ at box 104, and uses all of the measured isolation resistances, stack voltages and battery voltages in equation (2) to calculate the stack coolant resistance $R_{pcs}$ at box 106. The process then calculates the coolant conductivity at box 108 for the specific design of the system, where the voltage potential of the column of coolant is obtained for the resistance calculated. The process ends at box 110.

It is noted that the process discussed above puts the fuel cell system in a high power condition and a low power condition to make the voltage measurements to get the different ratios between stack voltage and battery voltage. However, when those system conditions are provided and when the calculations are made can be application specific in that the process may wait for the fuel cell system to go into a high power mode and a low power mode, during, for example, a drive cycle, and make the measurements during those times. Thus, in one embodiment, it is anticipated that the diagnostic for determining the fuel cell stack coolant positive to chassis isolation resistance $R_{pcs}$ will be obtained while the vehicle is being operated in a periodic manner, and if it is determined that the isolation resistance $R_{pcs}$ is too low, then a warning can be given to the vehicle driver for service.

As will be well understood by those skilled in the art, the several and various steps and processes discussed herein to describe the invention may be referring to operations performed by a computer, a processor or other electronic calculating device that manipulate and/or transform data using electrical phenomenon. Those computers and electronic devices may employ various volatile and/or non-volatile memories including non-transitory computer-readable medium with an executable program stored thereon including various code or executable instructions able to be performed by the computer or processor, where the memory and/or computer-readable medium may include all forms and types of memory and other computer-readable media.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. An estimating system for calculating conductivity of a cooling fluid in a fuel cell system, said fuel cell system including a fuel cell stack electrically coupled to a stack bus and a battery electrically coupled to a battery bus, where the stack bus and the battery bus operate at different voltage potentials, said estimating system comprising a controller configured to provide:
    means for operating the fuel cell stack at a first stack operating voltage;
    means for measuring a first isolation resistance at the first stack operating voltage;
    means for measuring a first stack voltage at the first stack operating voltage;
    means for measuring a first battery voltage at the first stack operating voltage;
    means for operating the fuel cell stack at a second stack operating voltage that is different than the first stack operating voltage;
    means for measuring a second isolation resistance at the second stack operating voltage;
    means for measuring a second stack voltage at the second stack operating voltage;
    means for measuring a second battery voltage at the second stack operating voltage;

means for calculating a stack coolant resistance using the first and second isolation resistances, the first and second stack voltages, and the first and second battery voltages; and means for calculating the conductivity of the cooling fluid using the stack coolant resistance.

2. The estimating system according to claim 1 wherein the means for operating the fuel cell stack at a first stack operating voltage operates the fuel cell stack at a high stack operating voltage and the means for operating the fuel cell stack at a second power level operates the fuel cell stack at a low stack operating voltage.

3. The estimating system according to claim 1 wherein the means for measuring a first isolation resistance and the means for measuring a second isolation resistance measure a first and second positive to chassis isolation resistance between the battery bus and ground.

4. The estimating system according to claim 1 wherein the means for calculating a stack coolant resistance uses the relationship:

$$R_{pc_{PB}} = \frac{1}{\frac{1}{\left(\frac{V_b}{V_s}\right) \cdot R_{pcs}} + \frac{1}{R_{pcb}}}$$

for the first isolation resistance, the first stack voltage and the first battery voltage, and for the second isolation resistance, the second stack voltage and the second battery voltage, where $R_{pc_{PB}}$ is the measured isolation resistance, $R_{pcs}$ is a fuel cell stack coolant isolation resistance, $R_{pcb}$ is a battery bus isolation resistance, $V_s$ is the stack voltage and $V_b$ is the battery voltage.

5. The estimating system according to claim 4 wherein the means for calculating the stack coolant resistance uses the equation:

$$R_{pcs} = \frac{R_{pc_{PB1}} \cdot R_{pc_{PB2}}}{R_{pc_{PB1}} - R_{pc_{PB2}}} \cdot \left(\frac{V_{s2}}{V_{b2}} - \frac{V_{s1}}{V_{b1}}\right)$$

where $R_{pcs}$ is the stack coolant resistance.

6. The estimating system according to claim 1 wherein the means for measuring a first isolation resistance and the means for measuring a second isolation resistance measure a first positive to chassis isolation resistance and a second positive to chassis isolation resistance, where the chassis is a vehicle chassis.

7. The estimating system according to claim 6 wherein the battery bus is a propulsion bus on the vehicle.

8. The estimating system according to claim 1 wherein the fuel cell system is on a vehicle including a vehicle chassis.

* * * * *